United States Patent [19]

Fu et al.

[11] Patent Number: 4,826,557
[45] Date of Patent: May 2, 1989

[54] TAPE DISPENSER

[75] Inventors: Daivey Fu; Yung-Lang Tsai, Room D, 9th Floor, No. 19, Kuan Chien Road, both of Taichung City, Taiwan

[73] Assignee: Yung-Lang Tsai, Taiwan

[21] Appl. No.: 158,266

[22] Filed: Feb. 18, 1988

[51] Int. Cl.⁴ ............... B43M 17/00; B65H 19/00
[52] U.S. Cl. .................. 156/579; 156/523; 156/577
[58] Field of Search .............. 156/523, 527, 577, 579

[56] References Cited

U.S. PATENT DOCUMENTS

| 2,582,980 | 1/1952 | Fritzinger | 156/523 |
| 3,306,806 | 2/1967 | Seropian | 156/523 |
| 3,342,662 | 9/1967 | Grasmann | 156/523 |
| 4,486,263 | 12/1984 | Monzo Gomez | 156/579 X |

FOREIGN PATENT DOCUMENTS 2120678 12/1971 Fed. Rep. of Germany ...... 156/579

Primary Examiner—Michael W. Ball
Assistant Examiner—Steven D. Maki
Attorney, Agent, or Firm—Browdy & Neimark

[57] ABSTRACT

The present disclosure is related to an improved tape dispenser having a gun-shaped housing and operated by a trigger in operative association with a number of interconnected links so that a cutting blade disposed at the gun point can be actuated to laterally move for cutting off the rolled tape and smoothly dispensing the same simultaneously.

1 Claim, 2 Drawing Sheets

TAPE DISPENSER

SUMMARY OF THE INVENTION

The present invention provides for an improved tape dispenser, especially a kind of trigger-operated one. The trigger is in operative association with a linkage received in a gun-shaped housing, and actuated to produce a lateral movement of a cutting blade disposed at the gun point so that the extended tape can be cut off and simultaneously sticked to surface of a work piece with the help of a press roller mounted at the gun point.

The prior art tape dispensers make use of an elongate zig-zag cutting means disposed at the top of the tape projecting port, the outward extendable tape is properly pulled out and sticked to a work piece, then the tape is cut off from a rolled tape. Because the zig-zag cutting means is disposed above the press roller, the tip of the cut tape, sticked partially to a work piece, is not able to be continuously adhered to the same by way of the press roller, and further manual operation is required to complete the whole process. Such constitutes the central disadvantage of the conventional arts.

Therefore, the primary object of the present invention is to provide an improved tape dispenser having a gun-shaped housing which is equipped with a horizontally movable cutting blade and a cylindrical press roller both of which are disposed at the gun point of the housing and received therein so that the front section of a roll of tape accomodated within said housing can be smoothly outward extended and sticked to the surface of a work piece inch by inch by said press roller as long as the present tape dispenser is moved in a tape dispensing direction and a trigger means in association with a linkage receiving in said housing is actuated to move a cutting blade in a horizontal direction, when the gun shaped housing is held in a normal position, to cut off the extended tape from the rolled tape.

To better illustrate the present invention of its structure, operation mode and features, a number of drawings are given in company with a detailed description of the present invention.

DETAILED DESCRIPTION OF THE PREFERRED EMBODIMENT

Figure 1:
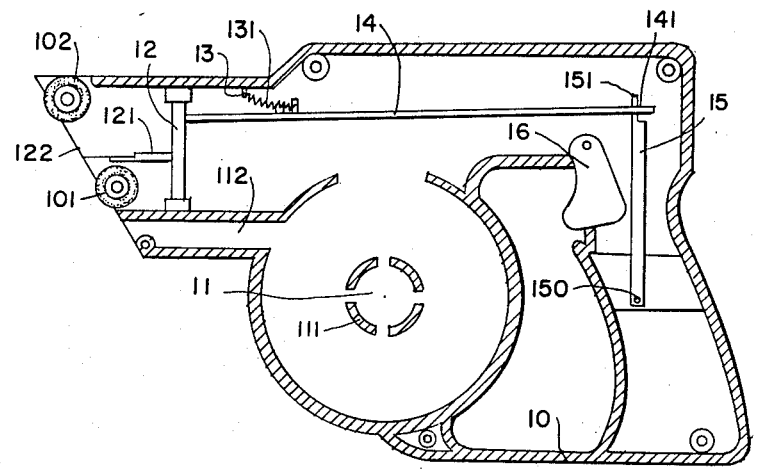
FIG. 1 is a longitudinal cross sectional view of the present invention.

As shown in FIG. 1, the present invention has a gun-shaped housing 10 with a circular tape container 11 extendingly disposed at the front of the grip handle of the housing 10 for the receiving of a roll of tape. At the center of said tape container 11 is disposed a center axle 111 for the mounting of a roll of tape, which is defined in a hollow cylindrical form, and the wall of the center axle 111 is divided into a number of separate pieces. A horizontally extended guide channel 112 projects from the wall of said tape container 11 for the passage of the outward extended tape.

Disposed right above the front end of the guide channel 112, is a guide roller 101 accompanied by another press roller 102, both of which are located inside the housing 10 and right at the gun point of the dispenser with a cutting blade 122 disposed therebetween which is horizontally movable by means of a rotatable axle 12.

Said press roller 102 is used to smoothly stick the dispensed tape to a work piece. The cutting blade 122 is fixedly mounted on a connecting piece 121 which is then fixed at the middle of a pivot axle 12 so that cutting blade 122 is able to move horizontally. The pivot axle 12 is vertically disposed behind the rollers 101, 102 and near the gun point of said gun shaped housing 10 as shown in FIG. 2.

A link 120 is horizontally extended from the upper section of said pivot axle 12, and the link 120 is further coupled to an elongate horizontal link 14 at the end thereof. The other end of said link 14 is engaged with a vertical link 15 by inserting the top end 151 thereof through a slot 141 disposed at the same end of said link 14. The lower end of said link 15 is fixed to the handle of the gun-shaped housing by a pin 150 which is served as a pivot center for said vertical link 15 when said trigger 16 is in contact association with the middle of the link 15 is actuated backward. Said trigger 16 is also pivotably fixed to the housing, as shown in FIG. 2.

An upright pin 142 is located near the front end of said horizontal link 14, and another pin 13, separated from said pin 142, extends from the top wall of said housing 10, and a spring 131 is disposed therebetween with two ends thereof secured on the two pins respectively.

Figure 2:
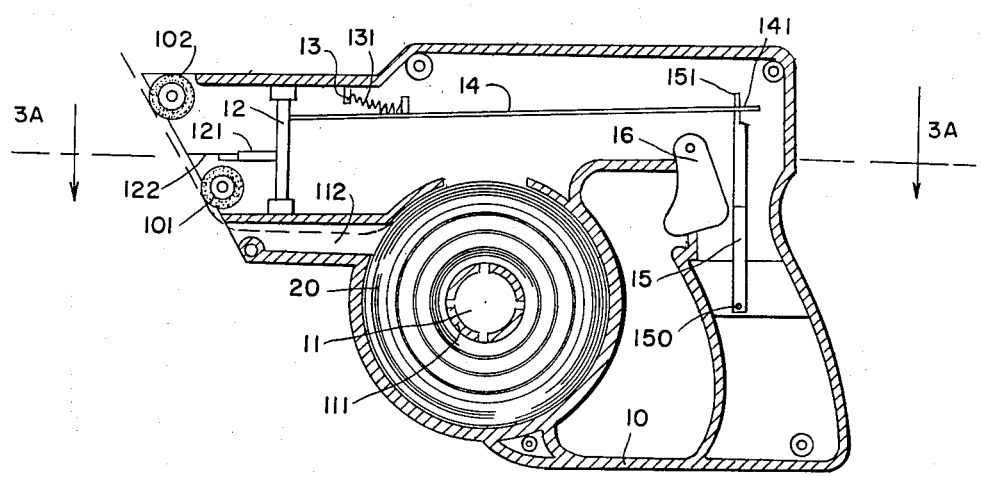
FIG. 2 is a longitudinal cross sectional view of the present invention showing a roll of tape being disposed within the present gun-shaped housing.
Figure 3A:
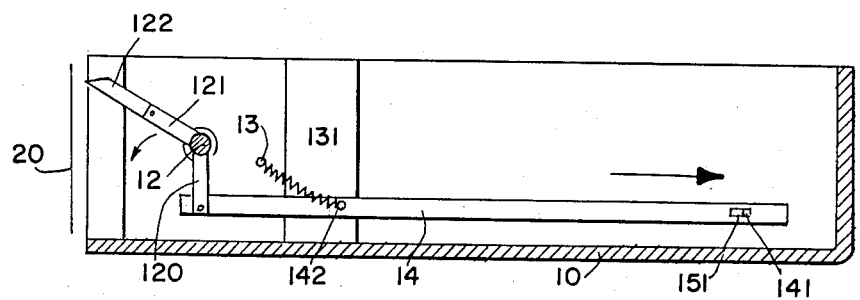
FIG. 3 consists of two lateral cross sectional views, taken along the line C—C in FIG. 2 and showing the movement of the linkage in said housing to actuate a horizontally movable cutting blade.
Figure 3B:
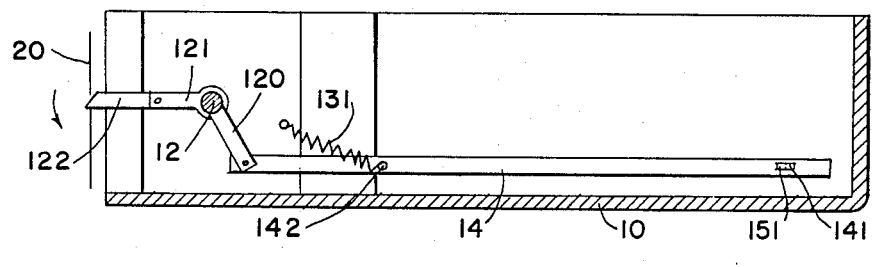

As shown in FIG. 2 and FIG. 3, a roll of tape 20 is first disposed in said tape container 11 with the central axle 111 going through the central hole of said roll of tape 20. The front extended portion of said roll of tape 20 is guided through the guide channel 112, then further extending via said guide roller 101, said cutting blade 122 and said press roller 102 respectively.

To use, the front tip of the rolled tape 20 is first sticked to a work piece and smoothly pressed by said press roller 102; with the drawing movement of said gun-shaped housing 10 by the hand of an operator, the roll of tape 20 is able to continue to dispense smoothly and stick to the surface of a work piece, and the press roller 102 is served to keep the dispensed tape firmly adhering to the work piece.

To cut off the extended tape 20, said trigger 16 is actuated. The actuation of said trigger 16 will clockwise pivot said vertical link 15, resulting in the right movement of said link 14; and the rightward movement of said link 14 will pivot said link 20 in a counter-clockwise direction as shown in FIG. 3, so does the upright axle 12 and the connecting piece 120; accordingly, the cutting blade 122 is pivoted in a horizontal plane within a limited range to effect the cutting of the dispensed tape.

The initiating position of the cutting blade 122 is slightly off the right edge of the to-be-cut tape, thus the lower edge of the cut tape resulting in a more smooth form. The unbroken edge of the tape can be easily broken by a slight force. And the release of said trigger 16 will make the present operative linkage resume its original position by way of said spring 131.

It becomes obvious now that by way of the proceeding detailed description of the operation of the present invention that the tape can be continuously dispensed and automatically stricked to the surface of the a work piece by way of said press roller 102 without the use of hand.

What is claimed is:

1. An improved tape dispenser comprising:
    a gun-shaped housing equipped with a trigger means disposed near the handle thereof;
    a circular tape container integrally disposed in fornt of said handle;
    a guide channel horizontally extended from the wall of said tape container;
    a guide roller disposed at the gun point of said gun-shaped housing;
    a press roller disposed slantly above said guide roller and also at the gun point of said housing;
    a cutting blade mounted on a vertical axle which is pivotally operated by a linkage means;
    said linkage means consisting of an elongate horizontal link to one end of which is connected a vertical link pivotally fixed at the bottom end thereof, the other end of said horizontal link being coupled to a horizontally extended link extending from said vertical axle, and said trigger means being in contact association with the middle of said vertical link so that the actuation of the trigger can accordingly result in horizontal movement of said cutting blade.

* * * * *